(12) United States Patent
Malmqvist

(10) Patent No.: US 6,451,258 B1
(45) Date of Patent: Sep. 17, 2002

(54) REACTION VESSEL, CASSETTE AND SYSTEM FOR PERFORMING BIOCHEMICAL REACTIONS

(75) Inventor: Mats Malmqvist, Uppsala (SE)

(73) Assignee: AlphaHelix AB, Uppsala (SE)

(*) Notice: Subject to any disclaimer, the term of this patent is extended or adjusted under 35 U.S.C. 154(b) by 0 days.

(21) Appl. No.: 09/424,540

(22) PCT Filed: May 28, 1998

(86) PCT No.: PCT/SE98/01017

§ 371 (c)(1),
(2), (4) Date: Apr. 18, 2000

(87) PCT Pub. No.: WO98/54292

PCT Pub. Date: Dec. 3, 1998

(30) Foreign Application Priority Data

May 28, 1997 (SE) ................................................ 9702005

(51) Int. Cl.[7] ............................ G01N 9/30; G01N 21/75
(52) U.S. Cl. ........................... 422/59; 422/72; 422/102; 436/45; 436/177
(58) Field of Search .................... 422/59, 72, 99, 422/100, 102; 436/45, 177, 180; 435/287.2; 494/16; 210/515, 360.1

(56) References Cited

U.S. PATENT DOCUMENTS 4,248,830 A * 2/1981 Kallies et al. .............. 422/100
4,883,760 A 11/1989 Heelies

FOREIGN PATENT DOCUMENTS

| EP | A1 0005979 | 12/1979 |
| WO | 9118110 | 11/1991 |
| WO | 9215597 | 9/1992 |

OTHER PUBLICATIONS

Derwent's abstract, No. 87–99848/14, week 8714, Abstract of SU 1250320 (attached) Aug. 15, 1986.

* cited by examiner

Primary Examiner—David A. Reifsnyder
(74) Attorney, Agent, or Firm—Birch, Stewart, Kolasch & Birch, LLP

(57) ABSTRACT

A reaction vessel includes a receiving portion and a capillary portion. The capillary portion has a first end having an opening in fluid connection with the receiving portion, and a second end closed by a plug portion formed as an integral one-piece member with the capillary portion. The capillary portion is optionally detachable from the receiving portion of the reaction vessel. The reaction vessel simplifies many processes involving small volume chemical reactions, such as Polymerase Chain Reaction (PCR) determinations.

15 Claims, 3 Drawing Sheets

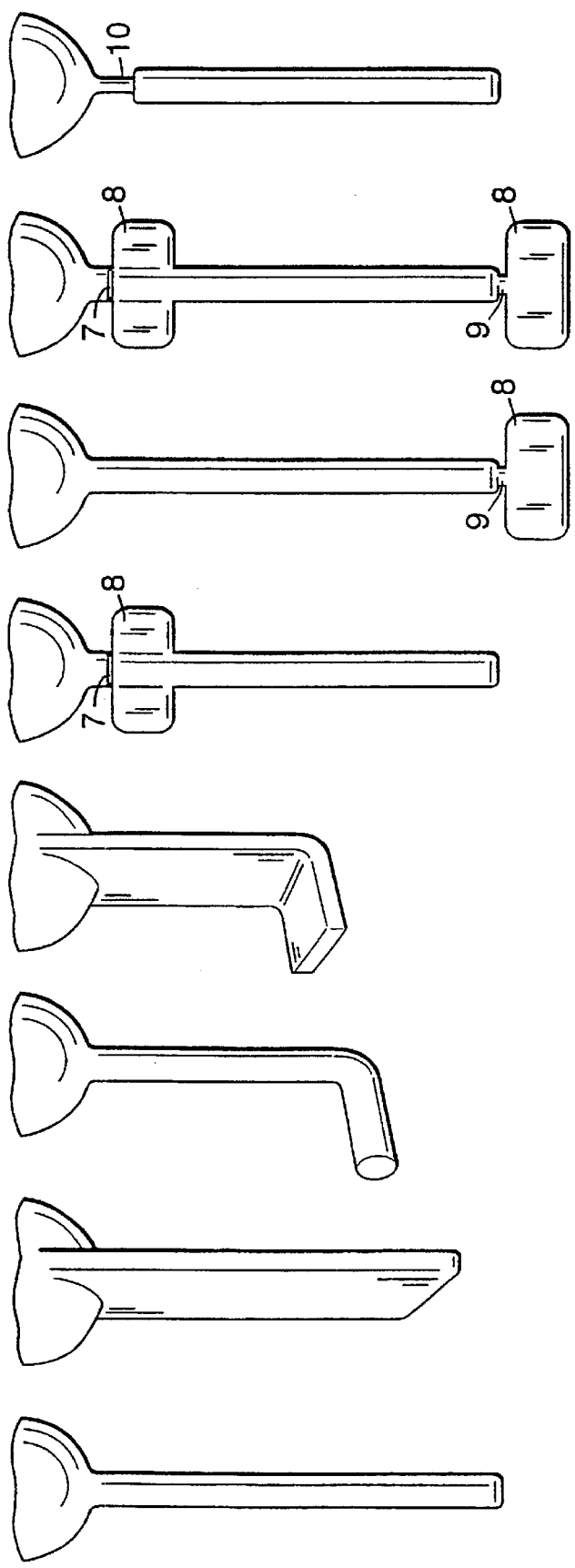

REACTION VESSEL, CASSETTE AND SYSTEM FOR PERFORMING BIOCHEMICAL REACTIONS

Figure 2:
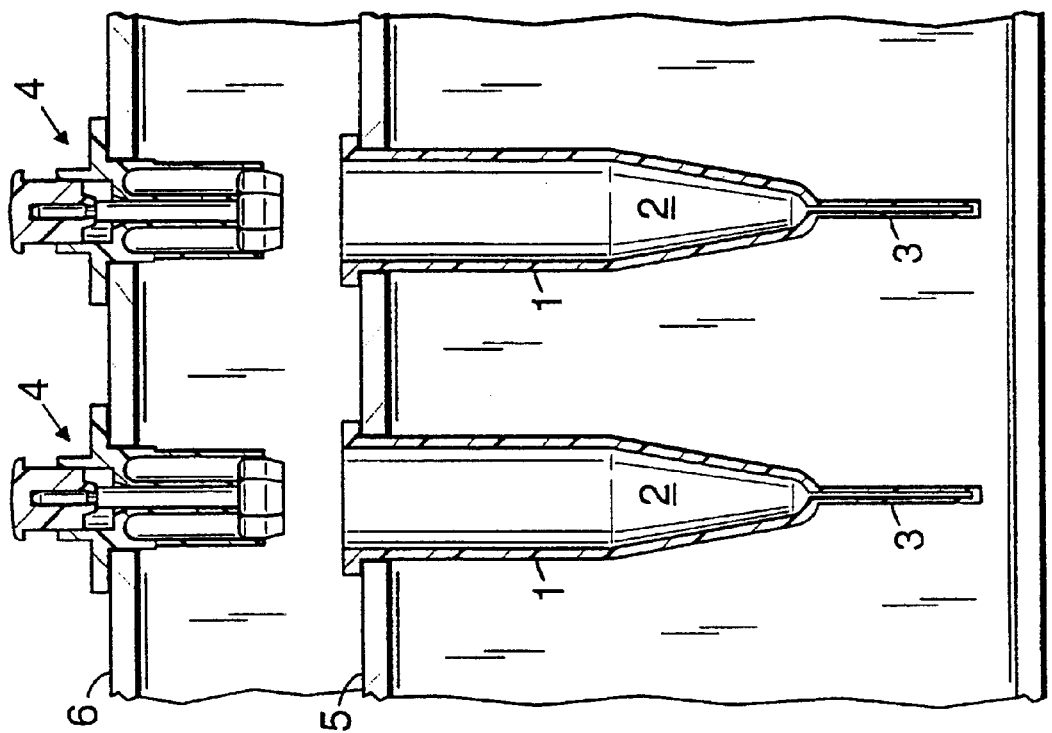

This application is the national phase under 35 U.S.C. §371 of PCT International Application No. PCT/SE98/01017 which has an International filing date of May 28, 1998 which designated the United States of America.

1. Field of the Invention

The present invention relates to a method to perform biochemical reactions and a new reaction vessel for use in said method. The invention is applicable for all small volume biochemical reactions in which the reagents are dispensed from reagent capillaries or so called reagent cartridges through centrifugation. The method and reaction vessel according to the present invention is particularly suitable for use in the PCR (Polymerase Chain Reaction) technique.

2. Prior Art

Biochemical reactions are routinely carried out in so-called microtiter plates—sheets of moulded plastic that typically contain eight rows and 12 columns of tiny wells, each of which capable of holding a few milliliters or less of the reaction mixture. Alternatively, 96 separate, detachable reaction vessels, e.g. micro centrifuge tubes or so called Eppendorf®—tubes or similar reaction vessels are arranged in the same manner. The 96-well format is widely used and the microtiter plates as such offers many benefits. Apparatuses are developed, which allow automatic and simultaneous handling of several microtiter plates, e.g. the automatic dispensing of reagents using pipetting robots and the simultaneous centrifugation in plate centrifuges.

An alternative to both manual dispensing and automatic dispensing using robots are dispensing devices, e.g. the reagent capillaries described in EP 530 283. In these, the reagents are predispensed in capillaries, separated from each other and from the ambient air, thus preventing untimely mixing and reactions and thus extending storage life. These capillaries are then brought in orientation with the reaction vessels or wells on a microtiter plate and emptied through centrifugation together with the reaction vessels. The commercially available Capilette® system (from Alphahelix AB, Sweden) exemplifies this application.

One widely used technique is the PCR (Polymerase Chain Reaction)-technique, which has found utility in a number of important diagnostic sectors. The PCR-method mainly comprises the following stages:

1) preparation of the reaction mixtures, i.e. preparation of the samples to be tested;
2) the actual amplification, i.e. the chain reaction in which the DNA molecules are replicated exponentially; and
3) the detection of positive samples by means of electrophoresis or hybridisation.

Using the PCR-technology, there are, however, several disadvantages with the presently available microtiter plates and reaction vessels. The PCR-method remains timeconsuming and work-intensive. The amplification steps, involving repetitive heating and cooling cycles, are carried out in capillaries. Capillaries are chosen to allow for rapid heating and cooling during the amplification cycles. The surface area in relation to the volume favours rapid heat transfer.

Normally such capillaries hold from about 5 $\mu$l to about 20 $\mu$l. The transfer of the reagent to the capillaries, followed by the necessary sealing of the capillaries, is a time-consuming step, additionally a step prone to contamination and errors. The capillaries are filled with the reaction mixture using the capillary force, i.e. one end of an open capillary is immersed in the reaction mixture. Thereafter one end of the capillary is sealed by melting one end in a gas flame. The capillary, filled with the reaction mixture and sealed at one end, is consequently subjected to the heating and cooling cycles to perform the amplification. For the handling of these capillaries, specific laboratory racks and apparatuses have been developed The object of the present invention is to simplify the handling of small volume reaction mixtures and to remove at least one source of errors and contamination. The present invention aims in particular to simplify the PCR-procedure. The present invention further aims to achieve the previous goals within the physical limits of the presently used 96 well format.

SUMMARY OF THE INVENTION

The present invention now discloses a new reaction vessel and a method to perform biochemical reactions according to the attached claims.

SHORT DESCRIPTION OF THE DRAWINGS

Figure 1:
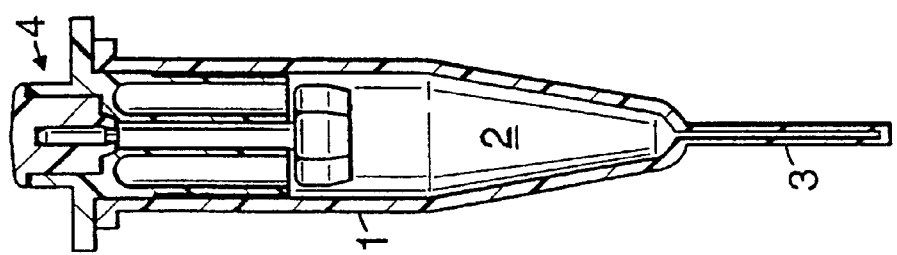
Figure 4:
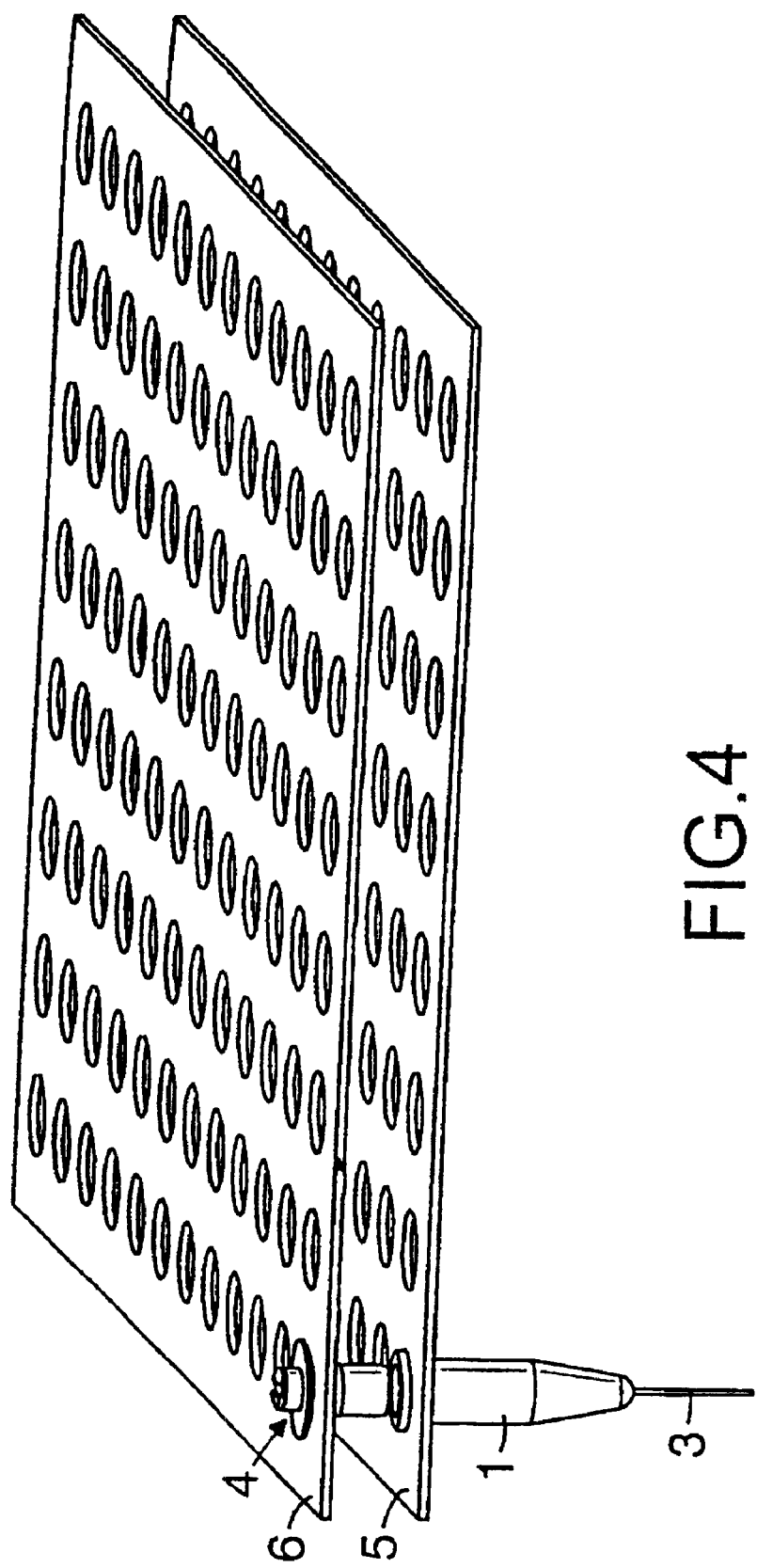

The invention will now be described in greater detail below with reference to the accompanying drawings in which FIG. 1 shows a cross-section of a reaction vessel according to the present invention, together with a reagent delivery system, attached to the vessel;

FIG. 2 shows schematically how reaction vessels according to the present invention, can be spatially arranged together with the reagent delivery systems;

FIGS. 3A through H depict various embodiments of the invention, where the capillary part of the inventive reaction vessel has different shapes; and FIG. 4 shows schematically how the inventive reaction vessels and corresponding dispensing device or delivery system can be arranged in the conventional 96-well format.

DESCRIPTION OF THE INVENTION

The drawbacks with current, conventional PCR technology can be alleviated thought the introduction of a reaction vessel and method according to the present invention. Said vessel and method are applicable also to other fields of small volume reactions, specially reactions where the risk of contamination has to be minimized.

The term "reaction vessel" is used in the following to denote any vessel, physically containing a liquid sample or reaction mixture, such as test tubes, micro centrifuge tubes, wells in microtiter plates etc. A reaction vessel according to the present invention can be manufactured in glass or in any suitable thermoplastic material meeting the requirements concerning chemical stability, resistance to deformation at elevated temperatures and optical qualities, i.e. allowing necessary measurements to be conducted through the material. Examples of suitable materials include, but are not limited to, polypropylene (PP), polystyrene (PS), polyethylene (PE), high density polyethylene HDPE, polycarbonate (PC), polyacetate (PA), poly methylene methacrylate (PMMA) and poly vinylidene fluoride (PVDF). The choice of material is not only governed by thermic, chemical and optical considerations, as noted above, but also by economical considerations such as material costs, production technology etc. One suitable method of production is injection moulding. Vacuum die-casting is an other possible method of production. Naturally, the reaction vessel is manufactured under conditions rendering it sterile and free from contaminants.

The term "small volume reactions" includes any chemical reaction, conducted in volumes below 100 μl. Typical biochemical reactions, intended to fall within this definition, are immunological determinations, histological determinations, enzymatical determinations, biochemical diagnosis of diseases, determinations of paternity, various determinations in forensic medicine, various operations in analysis and synthesis applications etc. Typical chemical reactions, intended to fall within this definition, are reactions in the screening and synthesis of pharmaceuticals, for example combinatorial chemistry, analysis, determination of environmental pollutants etc.

The diameter of the capillary portion can be continuous or, as is illustrated in FIG. 3 H, narrowed at its proximal end.

The present invention is illustrated in FIG. 1, where 1 denotes a reaction vessel, similar to a conventionally used micro centrifuge tube, e.g. a so called Eppendorf®—tube, but comprising a reagent receiving portion 2 and a capillary portion 3. The capillary portion is closed at its distal end. For illustrative purposes only, a capillary dispensing device 4 is attached to the reaction vessel. The reaction vessel is specially adapted to use in connection with such device. Nevertheless, it is not strictly limited to use in conjunction to such a device. However, the filling of the capillary is not possible without the aid of centrifugation thus making this combination a preferred one. Reagents added to the reaction vessel through a pipette, e.g. an automatic piston pipette, will not enter the capillary.

As a centrifugation step is necessary to transfer the reagents from the receiving portion of the reaction vessel to the capillary portion, it is preferred that addition of the reagents is performed in a step involving centrifugation or in close proximity to such a step. Preferably the reagents are added, using any suitable capillary device, emptied through centrifugation. The Capilette® system, manufactured by Alphahelix AB, Sweden is one example of such a system.

Whereas capillaries are normally filled using the capillary force, which require them to be open at both ends during filling, the capillary portion 3 according to the present invention is closed at its distal end, making it impossible to fill it other than through centrifugation. This is an unexpected and surprising approach, given that open capillaries have been filled and sealed since the introduction of the PCR technology, regardless of the additional work and contamination risks it entails. The use of conventional capillaries is motivated by a person skilled in the art, in that it makes possible considerably shorter heating and cooling times. Nevertheless, the drawbacks with conventional capillaries are acknowledged as serious. Seen in this light, the present invention satisfies a long felt need.

FIG. 2 shows schematically how the reaction vessels according to the present invention can be arranged in a plane, on a plate 5, comprising equally spaced openings. Preferably, said openings are arranged in eight rows with 12 columns in each, according to the conventional 96-well format. Correspondingly, the dispensing devices 4 are arranged in a similar fashion in a second plate 6, so that the dispensing devices can be brought in close contact with the reaction vessels before centrifugation and dispensing of their contents into the reaction vessels.

FIG. 3 A through H shows different embodiments of the present invention where the capillary portion has different shapes. The basic embodiment is a straight, mainly cylindrical capillary, with an uniform wall thickness throughout its length. (FIG. 3A). According to a preferred embodiment, illustrated in FIG. 3B, the capillary portion has a shape including two parallel surfaces, preferably a rectangular shape, making it suitable as a cuvette. The reaction mixture in the cuvette can then be subjected to determinations, e.g. spectrometric determinations of the extent of amplification achieved in the PCR-cycles.

FIG. 3C and D show embodiments, where the capillary portion has been deflected along an axis, forming an angle greater than 90° to the vertical axis of the reaction vessel. This deflection is made to better accommodate possible determinations as described above, made from below the reaction vessels. According to the state of the art, the progress of amplification can be monitored spectrophotometrically from above. To make these measurements possible, special covers with optically suitable properties have been suggested for the reaction vessels. Use of any device for dispensing the reagents, which device in or on the reaction vessel, will render this determination practically impossible. The bottom part of a conventional reaction vessel, for example a micro centrifuge tube, such as an Eppendorf®—tube, is unsuitable for such determinations made from below the vessel because of the uneven material thickness in this area. Using reaction vessels according to FIG. 3C and D, accurate measurements can be made also from below, for example by connecting sensors with optical fibres to locations, corresponding to the reaction vessels arranged in the 96-well format.

FIG. 3E shows an embodiment, where the capillary portion includes a notch or kerf 7, in the proximal part of the capillary portion e.g. immediately at the neck, adjoining to the receiving portion of the reaction vessel. The capillary portion can further include protruding handles or "ears" 8 facilitating the detachment of the said portion. As depicted in FIG. 3F, a similar notch and a removable plug with "ears" 8 can be arranged in the closed, distal end of the capillary portion. The lower removable plug is preferably integrated in the capillary portion, i.e. formed in the same material as the reaction vessel during moulding the entire reaction vessel. FIG. 3G shows an embodiment, where the capillary portion can be both detached from the receiving portion of the reaction vessel and opened at its distal end, to facilitate emptying. The details correspond to those, described previously in relation to FIG. 3E and F.

Finally, FIG. 3H shows an embodiment, where the capillary portion comprises an narrowed entry passage in its proximal end. This serves both to facilitate detachment of the capillary and to more precisely regulate the passage of reaction mixture into the capillary. A more narrow entry will also protect, after separation of the capillary portion, its contents from contamination and ambient air. By properly choosing the amount of sample and reagents in relation to the volume of the capillary portion, the oil or wax used to protect the reagents in the dispensing device, can now be positioned in the narrow neck, sealing the reaction mixture in the detached capillary.

The reaction vessel according to the present invention has the additional benefit, that solid particles, such as carrier particles, so called beads etc, are efficiently separated from the reaction liquid. Similarly, hydrophobic oils and waxes, possibly used to separate the reagents in dispensing capillaries, are separated from the reaction liquid. The present reaction vessel is also suitable for use in other small volume chemical reactions, such as in combination with the techniques of combinatorial chemistry.

The present invention further includes a method for performing small volume biochemical reactions, characterized in that the reagents are added to a vessel comprising a receiving portion and a capillary portion. The reaction mixture is forced to enter the capillary portion through centrifugation, which centrifugation is preferably also used to empty the reagents into the reaction vessel. Following the centrifugation, the reaction mixture in the capillary portion is subjected to heating and cooling cycles, either still integrated with the receiving part of the reaction vessel or detached from the same. Optical determinations to determine the progress of the desired reaction are performed through the capillary. An example of such a determination is the TaqMan™ Detection System, used for quantitation of nucleic acid sequences. This assay employs a fluorogenic probe, which consists of an oligonucleotide with both a reporter and a quencher dye attached. During PCR, a fluorogenic probe anneals specifically between the forward and reverse primer sites if and only if the target sequence is present. Sequentially, the probe is cleaved by the 5' nuclease activity of AmpliTaq DNA polymerase. Cleavage of the probe generates an increase in the fluorescence intensity of the reporter dye. This determination is suitable for use in combination with a reaction vessel and as a part of a method according to the present invention.

According to an embodiment of the invention, the capillary portion containing the reaction mixture is detached from the receiving part of the reaction vessel. Detaching or removing the capillary portion is facilitated by the notch 7 in FIG. 3E and G and by the narrow section 10 in FIG. 3H. The detached capillary part can then be subjected to further temperature cycles or determinations, stored or emptied. Storage stability of the capillary portion is enhanced by the narrowing 10 at the proximal end of the capillary, as shown in FIG. 3H and further enhanced if the sample and regent volumes are chosen so, that a layer of oil or wax is positioned in the narrow section. Emptying of the capillary portion is facilitated by opening it at its other end, employing the notch 9 and ears 8 depicted in FIG. 3G. Naturally the capillary portion can also be opened without prior detachment from the receiving portion, simply by opening the distal end, employing the notch 9 and ears 8 depicted in FIG. 3F or G.

In addition to the 96-well format, mentioned earlier in the description, this particular invention is naturally applicable also in other formats, specially in microtiter plates with a larger number of wells, such as the more recently developed 384-well format (16×24). The miniaturisation made possible by the present invention may prove especially favourable in applications, where more densely packed microtiter plates are used.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto.

What is claimed is:

1. A reaction vessel for performing small volume biochemical reactions using reagent cartridges which are emptied by centrifugation, the reaction vessel comprising a receiving portion and a capillary portion in fluid connection therewith, the capillary portion being closed at one end and open to the receiving portion at another end, the capillary portion at its opening to the receiving portion having a diameter of less than 1 mm, wherein the capillary portion is provided with a notch making it detachable from the receiving portion of said reaction vessel.

2. A reaction vessel for performing small volume biochemical reactions, said reaction vessel comprising:

a receiving portion; and a capillary portion having a first end and a second end, said first end having an opening in fluid connection with said receiving portion, said second end being closed by a plug portion formed as an integral one-piece member with said capillary portion.

3. The reaction vessel according to claim 2, wherein said plug portion is located entirely within an outer periphery of said capillary portion.

4. The reaction vessel according to claim 2, wherein said plug portion is formed of the same material as said capillary portion.

5. The reaction vessel according to claim 2, wherein said opening in said capillary portion has a diameter of less than 1 mm.

6. The reaction vessel according to claim 2, wherein said first end of said capillary portion is provided with a notch making said capillary portion detachable from said receiving portion.

7. The reaction vessel according to claim 6, wherein said second end of said capillary portion is provided with a notch making said plug portion detachable from said capillary portion.

8. The reaction vessel according to claim 2, wherein said second end of said capillary portion is provided with a notch making said plug portion detachable from said capillary portion.

9. The reaction vessel according to claim 2, wherein said first end of said capillary portion is provided with a narrow section making said capillary portion detachable from said receiving portion.

10. The reaction vessel according to claim 2, wherein said capillary portion has a rectangular cross-section.

11. The reaction vessel according to claim 2, wherein said capillary portion is provided with a bent portion intermediate said first end and said second end.

12. The reaction vessel according to claim 11, wherein said bent portion is bent at an angle of approximately 90 degrees.

13. The reaction vessel according to claim 2, wherein said capillary portion has a circular cross-section.

14. A cassette of reaction vessels according to claim 2, wherein said reaction vessels are arranged on a plane in a number of rows and columns.

15. A system for performing small volume biochemical reactions, comprising the reaction vessel according to claim 2, and a capillary dispensing device receivable within said receiving portion of said reaction vessel.

\* \* \* \* \*